(12) United States Patent
Wilkes et al.

(10) Patent No.: US 8,212,104 B2
(45) Date of Patent: Jul. 3, 2012

(54) MODEL OF EXPERIMENTALLY INDUCED CHRONIC PAIN AND USES THEREOF

(75) Inventors: Denise M. Wilkes, League City, TX (US); Li-Yen M. Huang, Czcloeston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 317 days.

(21) Appl. No.: 12/384,615

(22) Filed: Apr. 7, 2009

(65) Prior Publication Data

US 2009/0257955 A1    Oct. 15, 2009

Related U.S. Application Data

(60) Provisional application No. 61/123,797, filed on Apr. 11, 2008.

(51) Int. Cl.
*A01K 67/00*    (2006.01)
(52) U.S. Cl. .................................. 800/9; 800/8
(58) Field of Classification Search ........................ None
See application file for complete search history.

(56) References Cited

U.S. PATENT DOCUMENTS

| 7,015,371 | B2 | 3/2006 | Romans |
| 7,388,124 | B2 | 6/2008 | Romans |

OTHER PUBLICATIONS

Dolan et al. (2003). Upregulation of metabotropic glutamate receptor subtypes 3 and 5 in spinal cord in a clinical model of persistent inflammation and hyperalgesia. Pain. 106:501-512.*
Lee et al. (2000). An animal model of neuropathic pain employing injury to the sciatic nerve branches. NeuroReport. 11:657-661.*
Reilly et al. (2007). Posture, gait and the ecological relevance of locomotr costs and energ-saving mechanisms in tetrapods. Zoology. 110:271-289.*

* cited by examiner

*Primary Examiner* — Christine J Saoud
*Assistant Examiner* — Jon M Lockard

(57) ABSTRACT

Methods for producing peripheral nerve injury in sheep are provided. The sheep model provides a model of persistent neuropathic pain in humans. Methods for drug delivery are provided. Also provided is a method for screening potentially therapeutic agent for the treatment of persistent neuropathic pain. Also provided are the methods for measuring the changes produced by neuropathic pain.

6 Claims, 7 Drawing Sheets

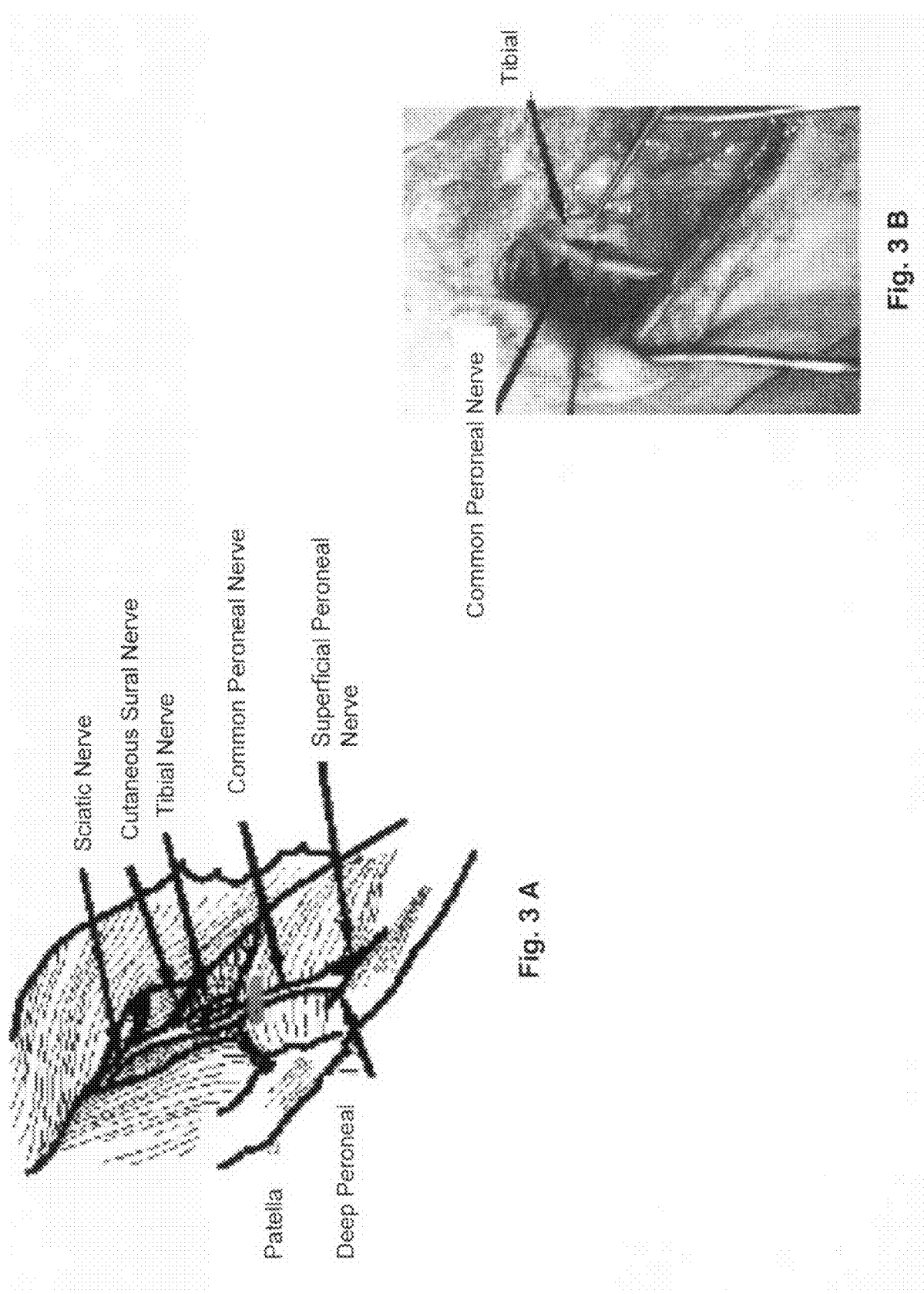

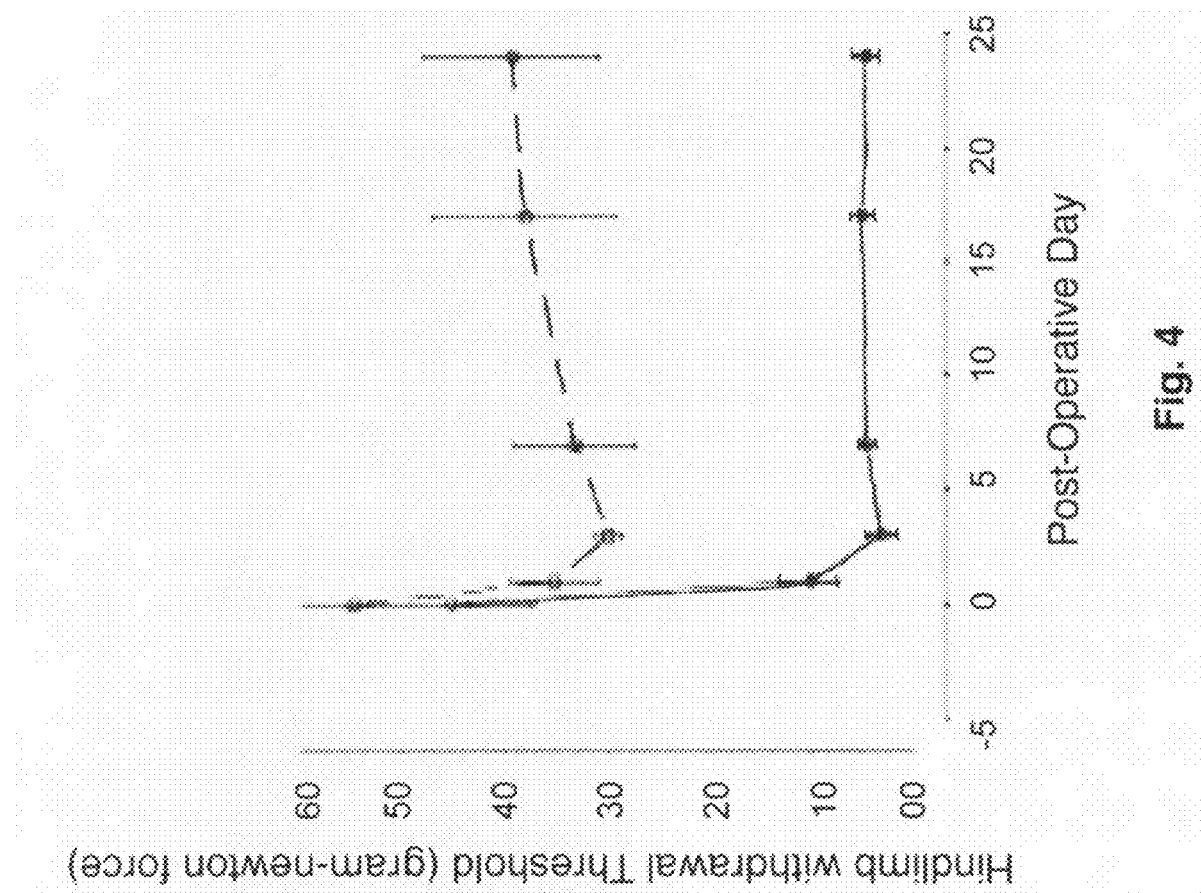

MODEL OF EXPERIMENTALLY INDUCED CHRONIC PAIN AND USES THEREOF

CROSS REFERENCE TO RELATED APPLICATION

This non-provisional application claims benefit of provisional application U.S. Ser. No. 61/123,797 filed on Apr. 11, 2008, now abandoned.

BACKGROUND OF THE INVENTION

1. Field of the Invention

The present invention relates generally to the fields of molecular neurology and animal models of pain. More specifically, the present invention discloses a sheep model of neuropathic pain behavior and uses thereof.

2. Description of the Related Art

The prevalence of chronic pain is common and will continue to grow due to the increase in the aging population. Chronic pain consists of either nociceptive or neuropathic pain or both. Neuropathic pain is caused by a lesion in the peripheral nerve and/or dysfunction of the central nervous system which produces symptoms often described by patients as burning, tingling, hot stabbing and shock-like in the absence of nociceptive stimulus.

There are many causes of neuropathic pain. Even though there is no universal classification system, neuropathic pain can be divided into categories based on etiologies and anatomy such as trauma (spinal cord injury, amputation), infection (herpes zoster, HIV), and compression syndromes (radiculopathy, carpel tunnel)[1]. Diagnosis based treatments have shown relative effective relief of neuropathic pain based on randomized controlled trials[2]. Application of results showing successful treatment of one etiology of neuropathic pain hasn't been reliably applied to another. A survey of 602 patients with neuropathic pain reported that these patients visited their physician more frequently reporting substantial pain interfering with their daily functioning despite receiving treatment[3]. Evidence suggests that the current diagnosis based treatments for neuropathic pain conditions are inadequate.

An increasing interest in pain research has been to develop treatments of neuropathic pain based on mechanisms instead of a diagnostic approach[4,5]. A mechanistic approach might provide more effective treatments. Much of the current knowledge of the mechanisms of neuropathic pain is based on animal models. Established animals models used in preclinical trials include selective spinal nerve ligation, sciatic loose ligature model, or spared nerve injury of the sciatic nerve in rat[6-8]. These rat models provide an economical way to elucidate pathways and mechanisms of neuropathic pain.

Although the rat models might be limited in predicting efficacy and safety in clinical trials because of several factors: the size difference between rats and humans, the lack of genetic diversity of inbred strains, and the relatively short lives which might limit the measurement of longitudinal effects. However, lack of available large mammalian model limits the ability to study efficacy and safety of therapeutic alternatives prior to clinical trials.

The sheep as a large-scale animal is advantageous due to its docile behavior, available and economical husbandry, and relative ease of training. The sheep is an attractive animal model for several reasons. Sheep have been used in research since the 1600's. Researchers have used sheep to study fetology, scrapie, asthma, viral diarrhea, spinal hardware, intrathecal drug delivery, and acute pain models.

In 1975, one of the first researchers to describe a method to quantify the mechanical stimuli in sheep was Lebeaux[9]. He described a method to measure the behavioral response to mechanical stimuli in restrained sheep. This method involved placing the sheep in a sling, which allowed movement of the legs and delivering a pinch with allis forceps to specific dermatomes. The response was limb withdrawal and/or a sign of generalized sensation and this was used to assess sensory loss produced by intrathecal or epidural local anesthetics. This study showed that pain and sensation could be qualitatively measured but failed to quantify the behavioral response. This failure was most likely due to a non-reproducible stimulus. Therefore, this method is only suitable for describing the gross changes in sensation.

Another sheep model described a method of delivering a quantifiable mechanical stimulus[10]. The mechanical stimulus was delivered by a device that utilizes pneumatic-driven pins to place pressure on the distal forelimbs and the evoked response was a forelimb withdrawal. A major disadvantage of this method is that it requires a fabricated device to produce pressure on forelimbs, which might increase variability among researchers. Another disadvantage is that the acute pain state was brief and required re-stimulation for each behavior measurement.

Sheep models have also been used to study spine stabilizing hardware, pharmacology of implantable intrathecal delivery devices, and nociceptive pain[10-12]. Sheep models have also been used extensively to study intrathecal drug delivery in pre-clinical trials. Since the size of the sheep spine is similar to humans, this also allows the use of commercially available intrathecal drug delivery devices.

SUMMARY OF THE INVENTION

The present invention describes a sheep model of neuropathic pain behavior, which involves transection of the common peroneal nerve. An advantage of a sheep model is that the sheep spine closely approximates the size and dimensions of the human spine, which allows the use of existing clinical delivery systems. The sheep model also allows testing of equivalent weight-based drug doses. Behavioral changes, mechanical allodynia and hyperalgesia, were assessed by hindlimb withdrawal thresholds using von Frey filaments and pin-pricks, respectively.

The present invention overcomes many of the failures of previous methods of pain research and pain models. In particular, the present invention provides for the first time a large mammalian neuropathic pain model. There exists numerous neuropathic pain models in rodents, which differ greatly from human in weight based dosing of medications.

An object of the invention is a method for the testing and/or screening of treatments for efficacy in the treatment of neuropathic pain.

Another object of the invention is a method for developing a treatment for neuropathic pain in humans, which comprises screening treatments by the method of the present invention.

An advantage of the invention is that one can use commercially available drug delivery devices and the presence of a persistent neuropathic pain state, which is ideally suitable for testing efficacy of drugs for neuropathic pain.

Thus, in one embodiment, the present invention is directed to a method for producing a non-human large mammalian model for persistent neuropathic pain with measured behavior, comprising the step of damaging the common peroneal nerve or a branch thereof in said non-human large mammal.

In another embodiment, the present invention is directed to a non-human large mammalian model for neuropathic pain, wherein a common peroneal nerve or branch thereof is damaged, resulting in the development of allodynia, thereby producing persistent neuropathic pain.

In another embodiment, the present invention is directed to a method of screening for an analgesic compound useful for the treatment of neuropathic pain, comprising the steps of: administering a test compound to the non-human large mammalian model for neuropathic pain of the present invention; exposing the model to a stimulus; and measuring the response to said stimulus, wherein a decrease in response to said stimulus indicates that said test compound is an analgesic compound useful for the treatment of neuropathic pain.

In certain embodiments, the present invention is directed to a method of screening for an analgesic compound useful for the treatment of neuropathic pain after nerve injury, comprising the steps of: administering a test compound to the non-human large mammalian model for neuropathic pain of he present invenion; measuring analgesic effect in the hindlimb that is on the same side (ipsilateral) as the damaged nerve; measuring the analgesic effect in the hindlimb that is on the opposite side (contralateral) as the damaged nerve; comparing the ipsilateral and contralateral measurements, wherein a lower analgesic effect in the ipsilateral limb as compared to the contralateral limb indicates that the analgesic compound loses potent after nerve injury. In some embodiments, measurement of the analgesic effect of the analgesic compound is performed three weeks after the peroneal nerve is damaged. In certain embodiments, measurement of analgesic effect is performed half an hour after the administration of the analgesic compound. In certain embodiments, the dose of the analgesic compound is from 2 to 1200 micrograms dissolved in 100 microliters of saline and injected intrathecally.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 2A shows the intrathecal catheter placement in the sheep model of the present invention. FIG. 2B shows externalization of the catheter port of the present invention.

FIG. 3A shows a peripheral nerve injury diagram whereas FIG. 3B depicts nerve exposure.

FIG. 4 shows the hindlimb withdrawal threshold. The solid line is the peripheral nerve injured side and broken line is the native side.

DETAILED DESCRIPTION OF THE INVENTION

Figure 1:
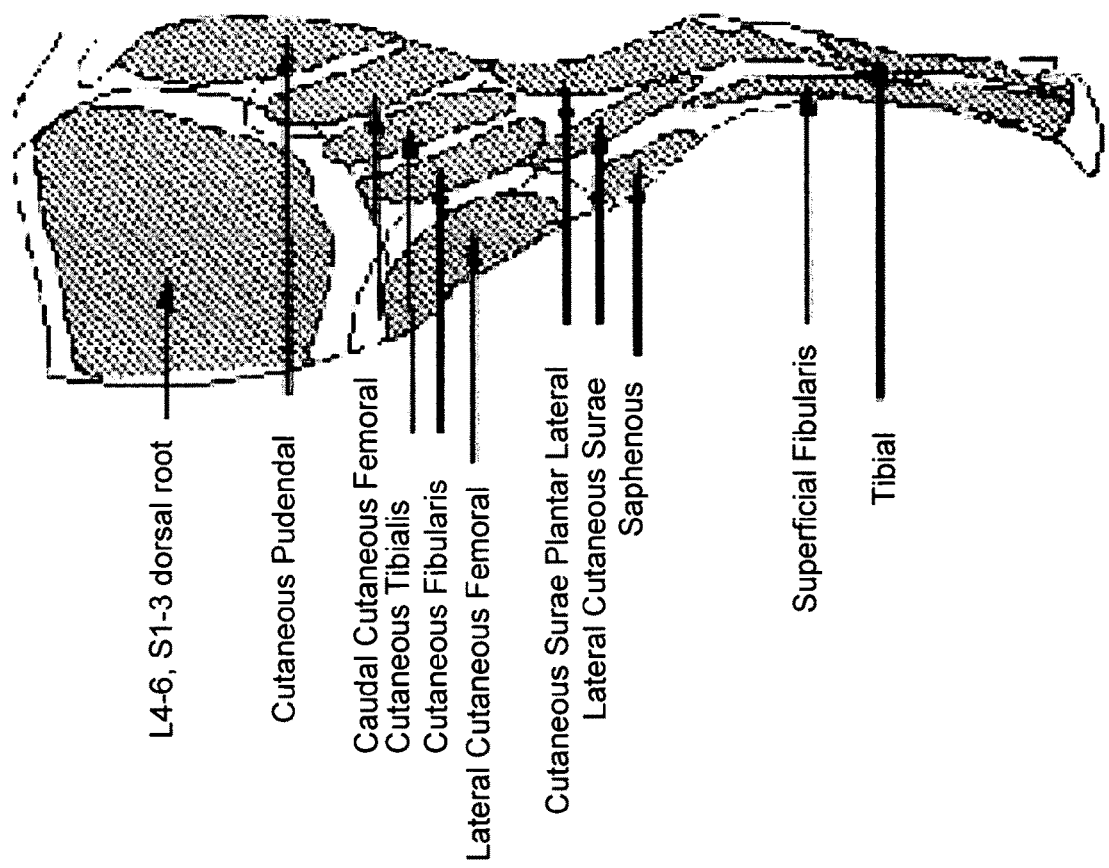
FIG. 1 shows the cutaneous innervation of sheep hindlimbs.

Thus, in one embodiment, the present invention provides a method for producing a non-human large mammalian model for persistent neuropathic pain with measured behavior, comprising the step of damaging the common peroneal nerve or a branch thereof in said non-human large mammal. The method may further comprising the step of applying a reproducible amount of force to elicit said measured behavior. Generally, the damage causes allodynia in said non-human mammalian model. Representative examples of means of causing said damage consists of surgical manipulation, including ligation, trans-section, compression, constriction, removal of a segment, and combinations thereof. Representative examples of non-surgical means of causing said damage including chemical, thermal, or radiative ablation and combinations thereof. Generally, the non-human large mammalian model includes ruminant mammals, canines, porcines, and felines. Preferably, the ruminant mammal is a sheep. One change in measured behavior consists of changes in sensory innervation adjacent to the nerve injury.

In another embodiment, the present invention provides a non-human large mammalian model for neuropathic pain, wherein a common peroneal nerve or branch thereof is damaged, resulting in the development of allodynia, thereby producing persistent neuropathic pain. Representative examples of means of causing said damage consists of surgical manipulation, including ligation, trans-section, compression, constriction, removal of a segment, and combinations thereof. Representative examples of non-surgical means of causing said damage including chemical, thermal, or radiative ablation and combinations thereof. Generally, the non-human large mammalian model includes ruminant mammals, canines, porcines, and felines. Preferably, the ruminant mammal is a sheep. One change in measured behavior consists of changes in sensory innervation adjacent to the nerve injury.

In another embodiment, the present invention provides a method of screening for an analgesic compound useful for the treatment of neuropathic pain, comprising the steps of: administering a test compound to the non-human large mammalian model for neuropathic pain of the present invention; exposing the model to a stimulus; and measuring the response to said stimulus, wherein a decrease in response to said stimulus indicates that said test compound is an analgesic compound useful for the treatment of neuropathic pain.

In certain embodiments, the present invention is directed to a method of screening for an analgesic compound useful for the treatment of neuropathic pain after nerve injury, comprising the steps of: administering a test compound to the non-human large mammalian model for neuropathic pain of the present invention; measuring analgesic effect in the hindlimb that is on the same side (ipsilateral) as the damaged nerve; measuring analgesic effect in the hindlimb that is on the opposite side (contralateral) as the damaged nerve; comparing the ipsilateral and contralateral measurements, wherein a lower analgesic effect in the ipsilateral limb as compared to the contralateral limb indicates that the analgesic compound loses potent after nerve injury. In some embodiments, measurement of the analgesic effect of the analgesic compound is performed three weeks after the peroneal nerve is damaged. In certain embodiments, measurement of analgesic effect is performed half an hour after the administration of the analgesic compound. In certain embodiments, the dose of the analgesic compound is from from 2 to 1200 micrograms dissolved in 100 microliters of saline and injected intrathecally.

Animals

Adult female merino sheep weighing 40-60 kg were used to produce the peripheral nerve injury sheep model. All experimental procedures were approved by the Institutional of Animal Care and Use Committee at the University of Texas Medical Branch and were in accordance with the guidelines of National Institutes of Health and of the International Association for the study of Pain (IASP).

Intrathecal Catheter Placement

Sheep were fasted for 24 hours prior to surgery. General anesthesia was given followed by 600 mg IM injection of ketamine. An intravenous line was placed in the external jugular and the sheep received an additional 200 mg of ketamine IV and a prophylactic dose of cefazolin 1 g IV. After intubation, the sheep were maintained on 2% isoflurane in oxygen and mechanically ventilated. The sheep received IV fluids (0.9% Normal Saline). Body temperature was maintained with a circulating water pad. Oxygen saturation was monitored and maintained between 98-100%. Heart rate and blood pressure remained within normal limits and required no adjustments. Sheep was positioned prone with hind limbs positioned cephalad beside the abdomen. A positioning pillow was placed under the chest, raising the head and chest and allowing a lordotic curve of the lumbar spine. The sheep was loosely secured to the operating table. The lumbrosacral area was sterilely prepped with betadine and draped. A vertical midline incision was made over the L-6 to S-2 vertebrae. The spinous processes of L6 and S1 were partially resected to allow greater exposure of the dura. A purse string of 7-O nylon was placed in the dura, the dura carefully lifted and nicked. A RACZ epidural catheter (16 Ga×36) catheter with snaplock catheter/syringe adapter was placed into the subarachnoid space and advanced until the 10 cm mark was at the opening of the dura. Once CSF flow through the catheter was confirmed, the dura was pulled close to the catheter with the purse string and the catheter was secured to the muscle fascia. The dura, muscle fascia, and skin were closed. The catheter was looped and secured subcutaneously. The catheter was then tunneled and secured to the skin of the sheep with suture. The sheep was allowed 5 days to recover and was tested for neurologic deficits. Animals with neurologic deficits were sacrificed.

Common Peroneal Nerve Injury

After the placement of an intrathecal catheter and the documentation of a lack of any neurological deficits, common peroneal nerve injury surgery was performed. As described previously, the sheep was premedicated with intramuscular ketamine, intubated and mechanically ventilated. The sheep was positioned laterally and the hind leg was sterilely prepared and draped. A vertical incision was made mid-thigh. The semimembranous and semitendinous muscle bellies were separated to expose the common peroneal nerve and tibial nerve. The common peroneal nerve was ligated with 2-0 silk suture and cut distally. A 1-cm segment was removed from the distal stump to prevent re-growth. Fascia and skin were closed.

Behavioral Studies: Mechanical Allodynia

The behavioral test was conducted on sheep in raised stanchion with the animal facing away from the tester. The lateral aspect of the hind limb was shaved prior to testing. These stanchion allowed access to their hind limbs. After 30 minutes equilibration time in the testing room, behavioral tests were done as follows.

The lateral aspect of the hind limb was touched with the von fry filament perpendicular to the hind limb with sufficient force to cause a bend in the filament. A positive response was an abrupt withdrawal of the limb. Sufficient time was allowed to allow for resolution of any behavioral response to previous stimuli. The series of von frey filaments chosen followed the up-down method[13]. Basically, six von-frey filaments were chosen so that two were above the threshold and two below.

Based on the response to the first von-frey stimuli presented the following stimulus was increased if a negative or null response or decreased if there was a positive response. The 50% response threshold was calculated using the formula: 50% g threshold=$(10^{[x_f+\kappa\delta]}/10,000$. The 50% withdrawal thresholds to von-frey filaments were used to assess the behavior change. To avoid inter-observer variability, one investigator did the majority of behavioral experiments. Additionally, each sheep did only one behavioral test per day.

Mechanical Hyperalgesia

With the sheep in the stanchion, a pin-prick test was performed using a 300 gram von-frey filament. The lateral part of the hindlimb was briefly stimulated at intensity sufficient to indent but not penetrate the skin. The duration of hindlimb withdrawal was recorded[14].

Figure 6:
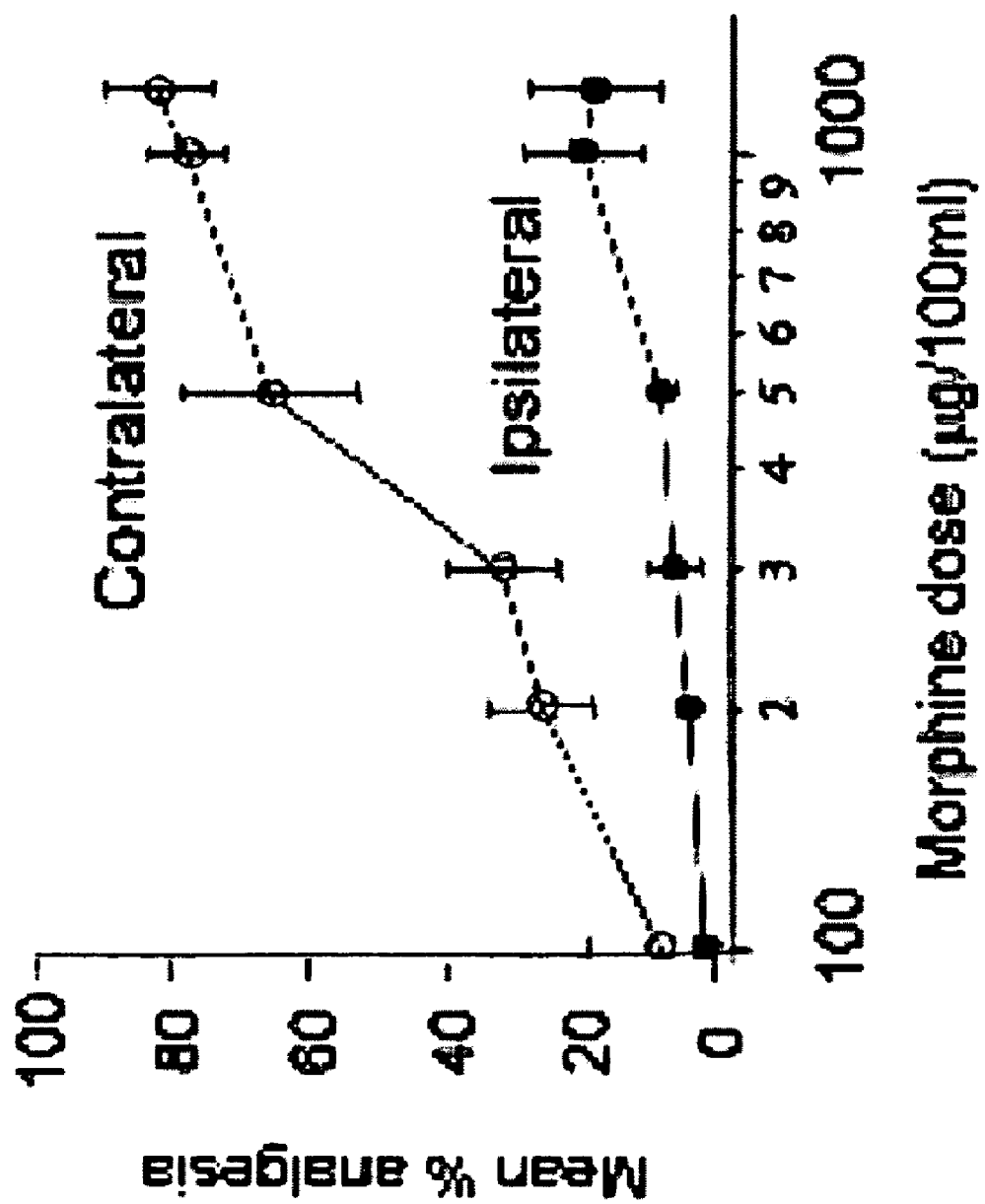
FIG. 6 shows morphine dose-response. Mean % analgesia is measured in both ipsilateral (nerve injured) and contralateral (non-injured) hindlimbs. The analgesic effect of morphine is significantly reduced after nerve injury.

Three weeks after peroneal nerve injury, the analgesic effect of morphine was measured. Increasing morphine sulfate doses, from 2 to 1200 micrograms, were dissolved in 100 microliters of saline and injected intrathecally. Mechanical hyperalgesia was tested in both the ipsilateral (nerve injured) and the contralateral (non-injured) hindlimb. Each measurement was taken 30 minutes after drug delivery. FIG. 6 shows the dose response curve of morphine in the ipsilateral and contralateral hindlimb. The ipsilateral compared to the contralateral dose response curve shows a reduction in potency by approximately 2-fold and a reduction in the efficacy by approximately 4-fold. Therefore, after nerve injury, morphine exhibits much less analgesia.

Microinjection of the Dorsal Root Ganglion Protocol

Figure 7:
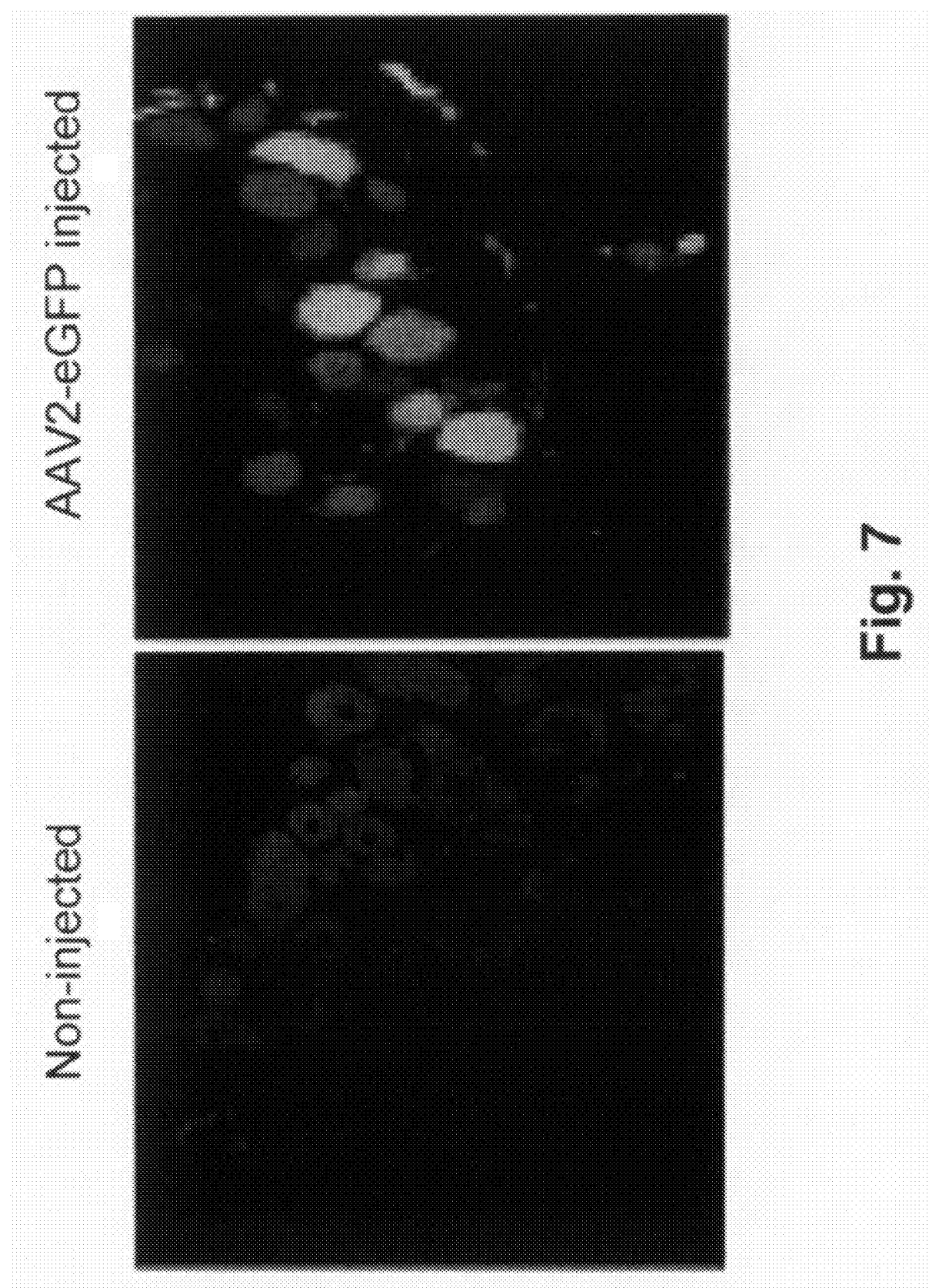
FIG. 7 shows expression of eGFP in paraformaldehyde-fixed sheep DRG tissue sections. eGFP expression shown in DRG injected with AAV2-eGFP compared to control DRG (non-injected) in tissue harvested 5 weeks after virus injection.

For dorsal root ganglion (DRG) injections, sheep were anesthetized with ketamine and maintained under general endotracheal anesthesia. The DRG was exposed using a partial laminotomy technique. Virus injection occurred over twenty minutes with a hamilton syringe secured to the spreading clamps. In order to develop infection methods, rAAV expressing enhanced green fluorescent protein (eGFP) were first used. Then these methods were used to express rAAV µ opioid receptor. After 8 weeks, the DRG was fixed, harvested, and sectioned. The fluorescence of the eGFP was detected with fluorescent microscopy and compared to non-injected DRG. Shown in FIG. 7 is the expression of eGFP in many dorsal root ganglia neurons. The DRG that was injected with virus is compared to the control (non-injected) DRG.

Intrathecal Morphine

Baseline withdrawal thresholds to mechanical stimulation were measured prior to morphine administration and at ten-minute intervals post-morphine. The anti-nociceptive effect of morphine time course was determined by measuring the pin-prick frequency every 10-min after intrathecal administration.

Results

Baseline behavioral studies were done prior to nerve injury or intrathecal catheter placement. Sheep were tested with von fry filaments as described. The sheep were tested on three different occasions. The sheep were always tested in a stanchion, which limited the movement of the sheep but allowed unrestricted movement of the legs (see FIG. 1A). One of two examiners performed all of the behavioral testing. The testing room doors were closed and had only one sheep in the room at a time. The cutaneous area tested with the von fry filaments corresponded to the cutaneous innervation of the sural nerve (cutaneous surae plantar lateral) located on the lateral side of the hindlimb (see FIG. 1B). Maintenance of these criteria for the testing environment was strictly followed.

All experimental animals were maintained in good health. The nerve injury animals were housed in solitary cages within general husbandry due to the concern that resident sheep would manipulate the intrathecal catheters. Sheep are herding animals and prefer close contact with other sheep. Therefore, the peripheral nerve injury sheep were kept within hearing range and sight of the general sheep population. The peripheral nerve injury sheep tolerated solitary housing without signs of distress. The sheep gained weight normally during the test period.

An intrathecal catheter was placed to provide a drug delivery route that allowed drugs to be easily titrated to highly efficacious levels while not requiring special animal care by animal facility staff. An additional problem encountered was that in the merino sheep, the spinal cord terminated in the sacrum, which increased the risk of spinal cord damage during catheter placement. In order to ensure a lack of neurological damage, baseline behavioral testing was completed prior to placement of the intrathecal catheter and sheep were monitored for neurologic changes for 5 days after catheter placement. Any sheep that demonstrated neurologic deficits were then euthanized. The catheters were placed through a nick in the dura under direct visualization in order to further safeguard against spinal cord damage. The catheters were tunneled and sutured to the skin and remained in place for the duration of the experiment.

Figure 2:
FIGS. 2A-2B show placement of the catheter in the model of the present invention.
Figure 2:
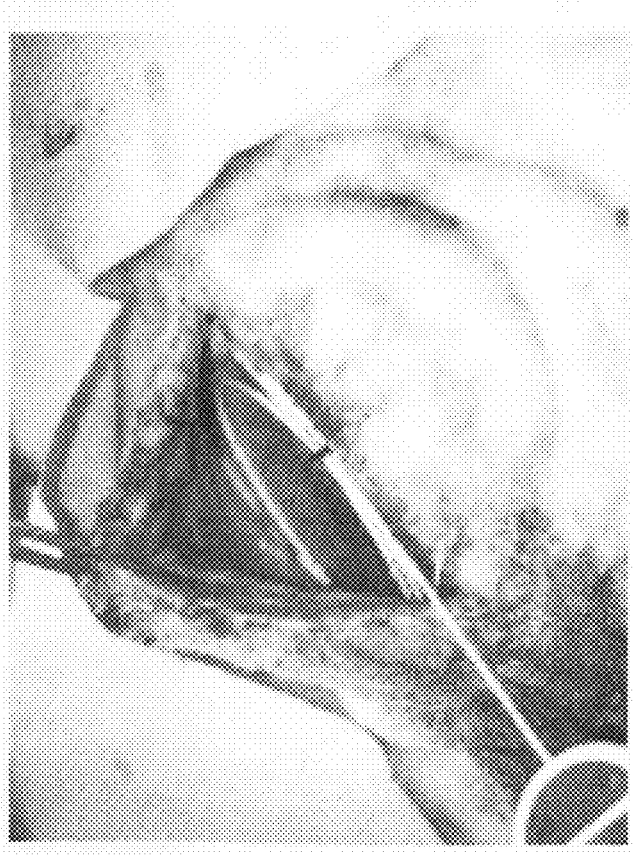

FIG. 2 shows the catheter sutured onto the dura with excess catheter coiled subcutaneously with the access port sutured to the skin. The intrathecal catheters remained in place without significant displacement and remained patent for 6 weeks. The sheep received routine animal care. The only modification was that they were housed separate to prevent resident sheep from tampering with the catheters. The sheep were then tested with von-fry filaments to examine if the placement produced behavioral change. No behavioral change was observed when compared to baseline behavioral studies.

The sheep recovered quickly after peripheral nerve injury surgery and within an hour after extubation were standing and walking. The peripheral nerve injury produced sensory and motor changes grossly observable the next day. The sheep avoided physical contact on injured side and was observed to shake the overlying wool and lick injured hindlimb when lightly touched. All sheep showed a consistent deformity after peripheral nerve injury consisting of plantarflexion of the phalanges. In other words, the peripheral nerve injury model produced a sheep with weakness in dorsiflexion of its proximal phalanx. This resulted in the sheep supporting its weight on the metatarsals with the phalanges in plantarflexion. A thickened skin formed on the distal end of the metatarsals but didn't show signs of infection in any of the sheep throughout the experiment. The sheep was able to walk, run, and feed normally. Most importantly, the sheep was able to withdraw each hind limb equally. Sham sheep didn't exhibit any deformity.

The baseline withdrawal threshold (55±15 g) was considerably higher pre-surgery than after surgery (6±1 g). The mechanical withdrawal threshold in the peripheral nerve injury hindleg reduced dramatically in the first 5 days following nerve injury surgery. After day 5, the hindleg withdrawal threshold remained constant for the remaining 35 days of the study. The contralateral hindleg also shows a decline in the first 5 days after surgery but the withdrawal threshold remain 10-fold higher than the peripheral nerve injury withdrawal threshold.

Since morphine is the standard used to compare the analgesics, morphine was used to test the reversibility of tactile allodynia produced by the peripheral nerve injury model. The intrathecal route was chosen due to its increased analgesia compared to the intravenous route. Intrathecal catheters were placed as described above. Three weeks after peripheral nerve injury, the analgesic effect of morphine was measured. Morphine sulfate (50 to 1200 micrograms) was dissolved in 100 microliters of saline and intrathecally injected.

Figure 5B:
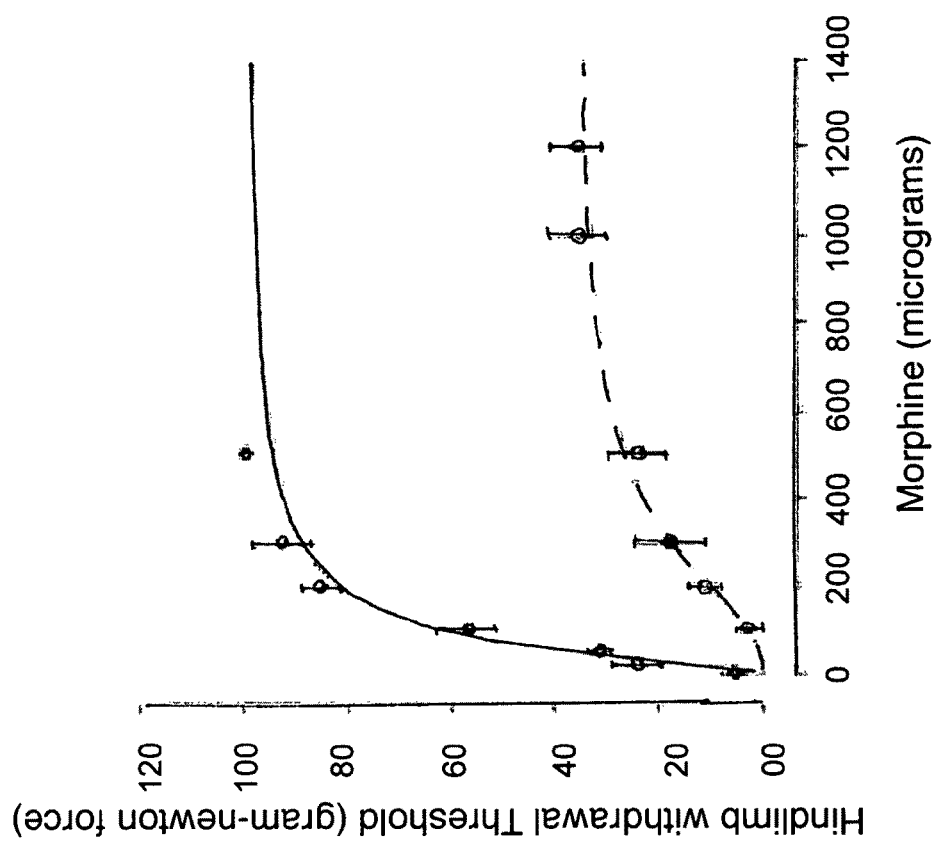
FIG. 5A shows the morphine time course where as FIG. 5B shows the morphine dose response; Pre-peripheral nerve injury (solid line) and post-peripheral nerve injury (dashed line)
Figure 5A:
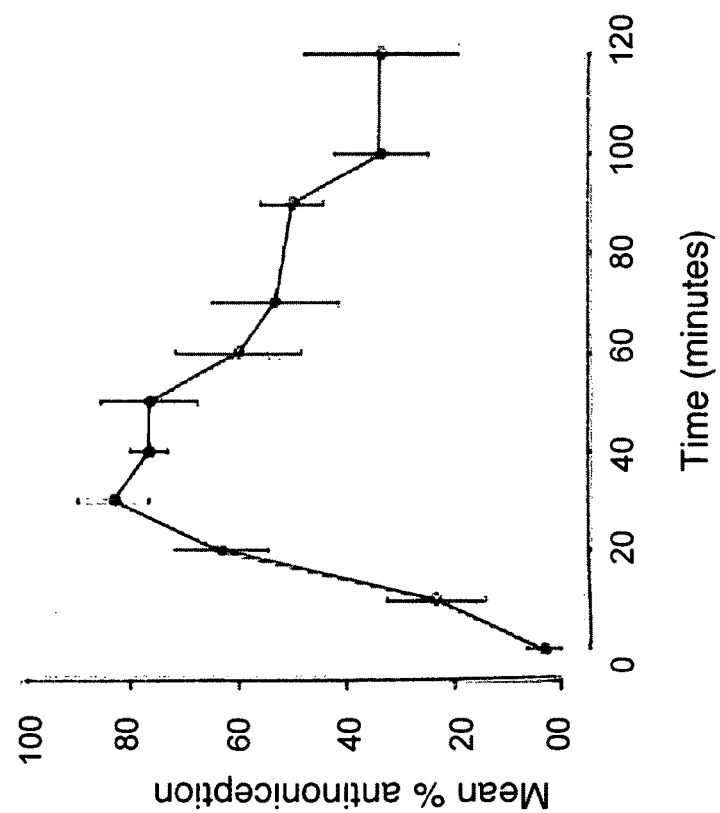

FIG. 5A shows the time course of analgesia from a dose of 200 micrograms measured by pin prick. Peak analgesia was observed at 30 minutes and duration extended beyond 120 minutes. FIG. 5B shows the analgesia as measured by pin prick comparing peripheral nerve injury and contralateral hindlimb. The analgesic effect of morphine shows more potency on the contralateral as compared to the peripheral nerve injury hindlimb. The hindlimb withdrawal threshold was completely reversed whereas the hindlimb withdrawal threshold on the ipsilateral hindlimb was only increased 36%. These results further confirm the patient's neuropathic symptoms and reports that the efficacy of morphine is low.

The method of the present invention produces a state of persistent pain that is constant over weeks. Therefore, the efficacy of drugs can be compared more accurately. Furthermore, this model employs commercially available von fry filaments to generate mechanical stimuli. These filaments have been used extensively in rodent behavior studies. The range of von fry delivered mechanical force (range newtons) describes the hindlimb withdrawal threshold in both normal and peripheral nerve injury sheep model.

Additionally, pain evoked behavior is distinct from normal sheep behavior. Sheep are able to move in the stanchion with some limitations. They are able to take one step forward and backwards, stand and lie down. They can raise, lower and look backwards with their head. During most of the testing time, the sheep were content with looking straight ahead and stand. After a mechanical stimulus was delivered, the hindlimb was withdrawn within 10 seconds and the sheep displayed the following behavior: the hindlimb skin was shook or flicked and/or the sheep turned its head around and looked at the area. After 20-30 seconds, the sheep returned to looking ahead and standing. Occasionally, a sheep would lie down. The sheep would be encouraged to stand which after the first 2 training sessions the sheep would stand and calmly looking forward.

REFERENCES

1. Waldman, Waldman, H., and Waldman, K. (ed. Waldman, S.) 268-278 (Saunders, Pa., 2007).
2. Finnerup, et al., Algorithm for neuropathic pain treatment: an evidence based proposal. *Pain* 118, 289-305 (2005).
3. McDermott, et al., The burden of neuropathic pain: results from a cross-sectional survey. *Eur J Pain* 10, 127-35 (2006).
4. Rowbotham, M. C. Mechanisms of neuropathic pain and their implications for the design of clinical trials. *Neurology* 65, S66-73 (2005).
5. Woolf, C. J. Dissecting out mechanisms responsible for peripheral neuropathic pain: implications for diagnosis and therapy. *Life Sci* 74, 2605-10 (2004).
6. Kim, et al., An experimental model for peripheral neuropathy produced by segmental spinal nerve ligation in the rat. *Pain* 50, 355-63 (1992).

7. Bennett, et al., A peripheral mononeuropathy in rat that produces disorders of pain sensation like those seen in man. *Pain* 33, 87-107 (1988).
8. Decosterd, I. & Woolf, C. J. Spared nerve injury: an animal model of persistent peripheral neuropathic pain. *Pain* 87, 149-58 (2000).
9. Lebeaux, M. Sheep: a model for testing spinal and epidural anesthetic agents. *Lab Anim Sci* 25, 629-33 (1975).
10. Nolan, et al., A. Techniques for comparison of thermal and mechanical nociceptive stimuli in the sheep. *J Pharmacol Methods* 17, 39-49 (1987).
11. Wilke, et al., Anatomy of the sheep spine and its comparison to the human spine. *Anat Rec* 247, 542-55 (1997).
12. Hassenbusch, et al., A sheep model for continuous intrathecal infusion of test substances. *Hum Exp Toxicol* 18, 82-7 (1999).
13. Nolan, et al., Investigation of the antinociceptive activity of buprenorphine in sheep. *Br J Pharmacol* 92, 527-33 (1987).
14. Tal, M. & Bennett, G. J. Extra-territorial pain in rats with a peripheral mononeuropathy: mechano-hyperalgesia and mechano-allodynia in the territory of an uninj s sured nerve. *Pain* 57, 375-82 (1994).

What is claimed is:

1. A non-human large mammalian experimentally induced model for chronic pain, wherein a common peroneal nerve of a ruminant mammal model, a canine model, a porcine model, or a feline model is damaged, resulting in the development of chronic pain behavior.

2. The model of claim 1, whereby said ruminant mammal is a sheep.

3. The model of claim 1, whereby said chronic pain behavior comprises mechanical allodynia, mechanical hyperalgesia, or thermal hyperalgesia.

4. The model of claim 1, whereby said damage is either surgical or non-surgical.

5. The model of claim 4, whereby said surgical damage comprises ligation, trans-section, compression, constriction, removal of a segment, or combinations thereof.

6. The model of claim 1, whereby said chronic pain behavior is neuropathic pain, inflammatory pain, or a combination of neuropathic pain and inflammatory pain.

* * * * *